United States Patent [19]

Dressel et al.

[11] Patent Number: 5,107,516
[45] Date of Patent: Apr. 21, 1992

[54] APPARATUS FOR CONTROLLED ABLATION BY LASER RADIATION

[75] Inventors: Martin Dressel, Goettingen; Harald Gerhardt, Rosdorf; Walter Neu, Goettingen, all of Fed. Rep. of Germany

[73] Assignee: Laser-Laboratorium, Gottingen, Fed. Rep. of Germany

[21] Appl. No.: 658,951

[22] Filed: Feb. 12, 1991

[30] Foreign Application Priority Data

Feb. 15, 1990 [DE] Fed. Rep. of Germany ....... 4004736

[51] Int. Cl.$^5$ ............................................... H01S 3/00
[52] U.S. Cl. ..................................... 372/109; 372/69; 372/57
[58] Field of Search ............................. 372/109, 57, 69

[56] References Cited

U.S. PATENT DOCUMENTS 5,005,180  4/1991  Edelman et al. ...................... 372/57
5,018,164  5/1991  Brener et al. ......................... 372/57

Primary Examiner—Leon Scott, Jr.
Attorney, Agent, or Firm—Iandiorio & Dingman

[57] ABSTRACT

Apparatus for controlled ablation of material from a predetermined working point, comprising a first laser, in particular excimer laser, for generating laser radiation pulses having a wavelength in a wavelength range suitable for the ablation, in particular in the ultraviolet spectral range, further comprising a radiation analyzer such as a spectrometer for analysis of material-specific radiation from the ablation plume forming at the working point, and a second laser, in particular a tunable dye laser, for generating a further laser radiation in a wavelength range which is different from said first wavelength range and which is better suited for the resonant stimulation of the radiation serving for the analysis than the ablation radiation wavelength range.

12 Claims, 1 Drawing Sheet

APPARATUS FOR CONTROLLED ABLATION BY LASER RADIATIONcFIELD OF THE INVENTION

The present invention relates to laser ablation, in particular an apparatus for controlled ablation of material from a predetermined working point.

DESCRIPTION OF THE RELATED ART

An apparatus comprising
- a laser for generating laser radiation pulses having a wavelength in a wavelength range suitable for ablation,
- a radiation analyzer,
- a first optical waveguide for transmitting laser radiation pulses from the laser to the working point and a second optical waveguide for transmitting radiation from a region in the vicinity of the working point to the radiation analyzer, is known from a publication by G. Laufer et al, Circulation 1988; 78: 1031-1039.

Apparatuses of the aforementioned type are used for example for angioplasty in the coronary and peripheral arteries. For generating short-wavelength laser radiation, in particular in the ultraviolet spectral range, which effects the ablation by non-thermal interaction with biological materials, excimer lasers have proved suitable, for example XeCl lasers (wavelength 308 nm, pulse duration 6-300 ns, repetition rate up to 500 Hz) or KrF lasers (wavelength 248 nm, pulse duration 10-100 ns, repetition rate for example 50 Hz). The laser radiation here can be guided via a multifibre catheter to the place of the intervention.

For clinical use it is absolutely essential to be able to make a reliable distinction between plaque and normal tissue during the ablation. It is admittedly known from the aforementioned publication of Laufer et al. that the tissue fluoresence in vitro, both on stimulation below the ablation threshold and during the ablation, exhibits recognisable differences between normal media, adventitia and soft and calcified plaque. These differences are however not very pronounced and therefore only limitedly suitable for clinical application. A particular problem is also the blood normally present at the working point in medical applications.

SUMMARY OF THE INVENTION

The present invention is based on the problem of further developing an apparatus of the type set forth at the beginning in such a manner that a more reliable distinction between the materials present at the working point is ensured.

The present invention is based on the recognition that the stimulation of the fluorescence radiation used for the analysis by the ultraviolet radiation serving for the ablation is not favourable because of the wide fluorescence spectra typical of complex organic compounds. In the apparatus according to the invention resonance fluorescence radiation is therefore stimulated by a laser radiation which is different from the laser radiation used for the ablation and the wavelength of which lies in an especially longer wave wavelength range more favourable for the resonance fluorescence stimulation. To generate the radiation stimulating the resonance fluorescence a laser tunable continuously over the entire visible and near infrared spectral range is particular suitable, more especially a dye laser, with which a resonant fluorescence of ablated materials of interest at the working point can be stimulated. For separate stimulation of the material-specific fluorescence a laser radiation pulse may be used which is radiated into the region of the working point simultaneously with the laser pulse effecting the ablation or preferably somewhat delayed, for example a few one-hundred nanoseconds, with respect to said pulse.

The present apparatus may be used for a great variety of purposes, for example controlled laser angioplasty by spectral analysis with a dye laser; surgical application for controlled cutting; laser lithotripsy; dental applications; material analysis at difficultly accessible points; analysis, in particular detection of pollutants in gaseous, liquid and solid materials; detection of corrosion at difficultly accessible points, and many others.

BRIEF DESCRIPTION OF THE DRAWINGS

Hereinafter some examples of embodiment of the invention will be explained in detail with the aid of the drawings, wherein.

DESCRIPTION OF THE PREFERRED EMBODIMENTS

Figure 1:
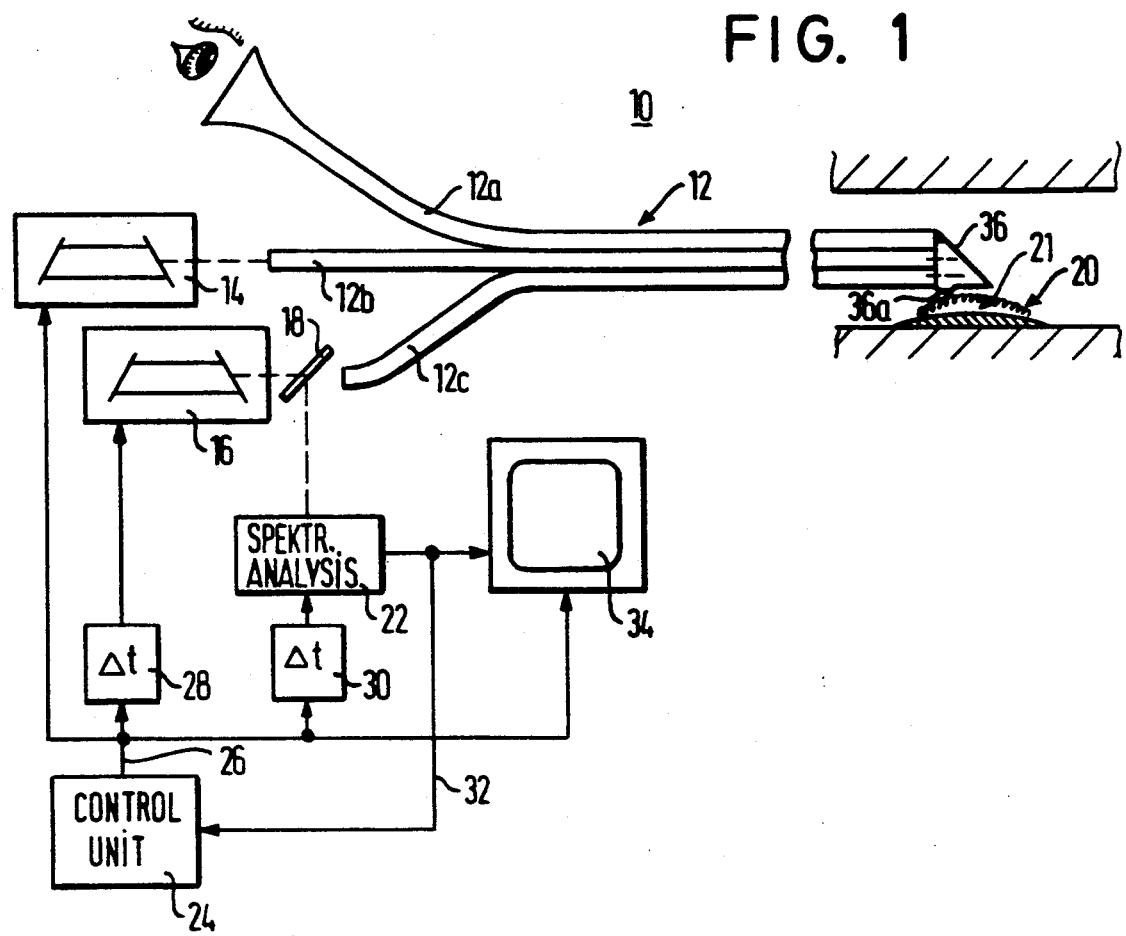
FIG. 1 shows an apparatus for controlled laser angioplasty according to one embodiment of the invention and FIG. 2 shows a modified part of the apparatus according to FIG. 1.

As example of one embodiment of the invention, in FIG. 1 an endoscopic apparatus 10 is illustrated which is particularly suitable for angioplasty but can of course also be used for other purposes in which a controlled laser beam working at a difficultly accessible point is necessary. The apparatus 10 includes an optical waveguide arrangement 12 comprising three optical waveguides 12a, 12b, 12c, in particular a coherent optical fibre bundle 12a and two incoherent optical fibre bundles or monofibres 12b and 12c. The coherent bundle 12a forms part of a conventional endoscope with which the working region can be visually observed. The optical waveguide 12b is coupled with its outer (left in FIG. 1) end optically to a first laser 14 which serves to generate the laser radiation, in particular ultraviolet radiation, the ablation. In the present example of embodiment the laser 14 is an XeCl excimer laser which furnishes laser radiation pulses with a pulse duration lying between 6 and 300 ns and a repetition rate of up to 500 Hz for a wavelength of 308 nm. The input end of the second optical waveguide 12c is coupled to a second laser 16 via a semitransparent possibly dichroic mirror 18 which transmits the radiation of the laser 16. The optical waveguide 12c or an additional waveguide also serves to transmit radiation from a region 20 in the vicinity of the working point (for example a plaque) in which the radiation of the laser 14 generates a gaseous ablation plume back to a radiation analyzer 22. The radiation emerging from the front end of the optical waveguide 12c is reflected by the semitransparent mirror 18 into the input of the radiation analyzer 22.

In the present example of embodiment the laser 16 is a pulsed dye laser which is continuously tunable over the entire visible and near infrared spectral range, i.e. for example from about 320 nm to 1.3 $\mu$m so that resonant transitions can be stimulated in atoms, molecules or ions and analyzed. The radiation analyzer 22 is a spectrometer or a monochromator and adjustable to a desired narrow spectral range or a desired resonance fluoresence line. It furnishes an electrical output signal which is a measure of the intensity of the radiation in the set spectral range.

The apparatus 10 further includes a control unit 24 which has an output 26 at which trigger pulses for the lasers are available. The trigger pulses are supplied directly to the laser 14 generating the UV radiation pulses including the ablation and are supplied to the laser 16 furnishing the longer-wavelength radiation pulses serving for the fluorescence stimulation and material analysis via a delay 28 by which the triggering of the radiation pulses of the laser 16 can be delayed with respect to the triggering of the radiation pulses of the laser 14 by a predetermined preferably adjustable period of time (in particular between 0 and 1 μs). If desired, the radiation analyzer 22 may also be clocked directly or via a delay generator 30.

In the laser ablation of plaques, by means of the second laser 16 it is possible for example to stimulate selectively one of the characteristic resonance lines of the calcium contained in the hard plaque, for example a line of the neutral calcium atom (CaI) at 422.7 nm or 657.3 nm or a line of the singly ionised calcium at 394.3 nm or 396.8 nm. In contrast to the wideband stimulation of the entire fluorescence spectrum the resonance fluorescence of the transition stimulated selectively by the dye laser is measured quantitatively on the same line, or as is easily possible for CaII on another line from the decay of the upper stimulated level (854.2 nm) and the calcium concentration calculated on-line therefrom. This makes it possible to distinguish the ablated materials and thus permits an in-situ control of the laser intervention. Complete ablation of plaques and thus specific elimination of a stenosis is therefore possible. Since the material removal is only a few μm per laser pulse, an undesired perforation of the vascular wall can also be avoided by an automatic control of the laser 14 as is indicated by a connection 32 of the output of the radiation analyzer 32 to the control unit 24. For visual monitoring of the ablation a monitor 34 may be provided which is connected to the output of the analyzer 22 and synchronized by the trigger pulses.

At the inner end of the optical waveguide arrangement 12 a radiation deflection element 36 may be provided, for example in the form of a prism with silvered hypotenuse. The prism may include a member 36a formed as lens and representing part of the endoscope.

Figure 2:
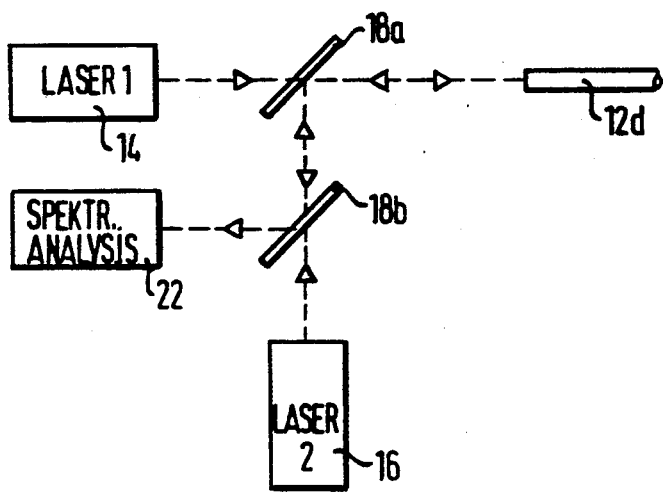

As FIG. 2 shows, a single optical fibre bundle or, as is preferred, a monofibre 12d suffices for the transmission of the radiation from the lasers 14, 16 to the working point and the transmission of the analyzing radiation ("analysis radiation") back to the analyzer 22. Two semitransparent mirrors 18a, 18b are then provided. The radiation from the first laser 14 enters the outer end of the optical waveguide 12d through the first semitransparent mirror 18a. The radiation from the second laser passes through a second semitransparent mirror 18b and is reflected by the first semitransparent mirror 18a into the optical fibre waveguide 12d. The radiation returning from the optical fibre waveguide 12d is first reflected by the mirror 18a, to the mirror 18b and then by the latter into the analyzer 22.

The optical waveguides 12b, 12c and 12d preferably consist of fused silica fibres. The end faces of monofibre optical waveguides may be selectively formed as lenses for beam divergence or beam focussing. For simpler beam conduction the end faces may also be formed with a taper extension (conical widening of the fibre). The ray paths for transmitting the radiation serving for ablation or other radiation treatment, the radiation generating the radiation used for the analysis and the radiation serving for the analysis may also be implemented by other optical waveguides or beam guiding systems.

We claim:

1. An apparatus for removing, by ablation, material from an object which includes said material, said apparatus comprising:
    first laser means (14) for generating laser radiation pulses having a wavelength in a first wavelength range suitable for removing said material from said object by ablation to produce ablated material;
    second laser means (16) for generating laser radiation having a wavelength in a second wavelength range suitable to induce resonance fluorescence in said ablated material producing resonance fluorescence radiation;
    radiation analyzer means (22) for analyzing the fluorescence radiation stemming from said ablated material; and
    optical radiation transmitting means (12,12d) for transmitting radiation, said radiation transmitting means including a first optical path to transmit said radiation pulses from said first laser means (14) to a location on said object from which material is to be removed to produce said ablated material in a volume (21) adjacent said location, a second optical path to transmit said radiation from said second laser means (16) to said volume (21) to induce resonance fluorescence, and a third optical path to transmit said resonance fluorescence radiation from said volume (21) of ablated material to said radiation analyzer means (22).

2. The apparatus of claim 1 wherein the radiation generated by said second laser means (16) has a longer wavelength than the radiation pulses generated by said first laser means (14).

3. The apparatus of claim 1 wherein said first laser means (14) generates radiation pulses having a wavelength in the ultraviolet range.

4. The apparatus of claim 1 in which said second laser means (16) further includes a tunable laser.

5. The apparatus of claim 1 in which said second laser means (16) further includes a dye laser.

6. The apparatus of claim 1 wherein said second laser means (16) generates radiation pulses.

7. The apparatus of claim 6, further comprising means (24, 28) for timing the radiation pulses generated by said second laser means (16) with respect to the laser radiation pulses generated by said first laser means (14).

8. The apparatus of claim 7 in which said timing means further includes an adjustable delay means for delaying generation of the pulses of said second laser means with respect to the pulses of said first laser means.

9. The apparatus of claim 1 wherein said radiation analyzer means (22) provides an output signal representative of the fluorescence radiation received from said volume, and wherein said first laser means is responsive to said output signal.

10. The apparatus of claim 1 in which said optical radiation transmitting means further includes an optical lightguide fibre.

11. The apparatus of claim 1 in which said optical radiation transmitting means further includes an optical lightguide fibre bundle.

12. The apparatus of claim 1 in which said optical radiation transmitting means further includes a mirror joint arm system.

* * * * *